United States Patent
Leysen et al.

[11] Patent Number: 5,994,366
[45] Date of Patent: Nov. 30, 1999

[54] TETRAHYDROIMIDAZO[2,1-A] ISOQUINOLINE DERIVATIVES

[75] Inventors: Dirk Leysen, Lommel, Belgium; Gerardus Stephanus Franciscus Ruigt, Oss, Netherlands

[73] Assignee: Akzo Nobel NV, Arnhem, Netherlands

[21] Appl. No.: 09/104,563

[22] Filed: Jun. 25, 1998

[30] Foreign Application Priority Data

Jun. 26, 1997 [EP] European Pat. Off. .............. 97201950

[51] Int. Cl.[6] ....................... A61K 31/47; A61K 31/505; C07D 471/04
[52] U.S. Cl. .......................... 514/292; 514/267; 544/252; 546/84; 546/81
[58] Field of Search ....................... 546/84, 81; 514/292, 514/267; 544/252

[56] References Cited

U.S. PATENT DOCUMENTS

| | | | |
|---|---|---|---|
| 3,624,093 | 11/1971 | Sulkowski | 260/288 R |
| 4,100,165 | 7/1978 | Houlihan | 260/288 CF |

OTHER PUBLICATIONS

Matechka D et al. J. Med. Chem. 39, 4704–4716, Nov. 1996.

M. Chaykovskyet et al., *Journal of Organic Chemistry*, 35:4:1178–1180, 1970.

*Primary Examiner*—Evelyn Mei Huang
*Attorney, Agent, or Firm*—Michael G. Sullivan; William M. Blackstone

[57] ABSTRACT

The present invention relates to certain tetrahydroimidazo[2,1-a]isoquinoline derivatives according to formula I

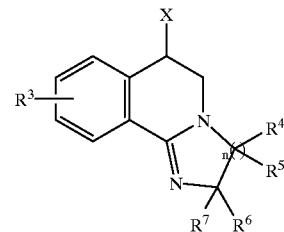
(I)

wherein X is a group (A) or (B)

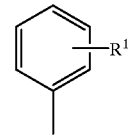

(A)

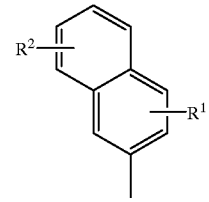

(B)

$R^1$, $R^2$ and $R^3$, which may be the same or different, each represent one or more substituents selected from hydrogen, $C_{1-6}$alkyl, $C_{3-6}$cycloalkyl, $C_{1-6}$alkoxy, $C_{1-6}$alkylthio, $C_{4-6}$cycloalkenyl, $C_{2-6}$alkenyl, $C_{2-6}$alkynyl and halogen;

$R^4$, $R^5$, $R^6$ and $R^7$, which may be the same or different, are each selected from hydrogen, $C_{1-6}$alkoxyC$_{1-6}$alkyl, $C_{4-6}$cycloalkenyl, $C_{2-6}$alkenyl, $C_{2-6}$alkynyl, $C_{3-6}$cycloalkyl and $C_{1-6}$alkyl; n is 1 or 2; or a pharmaceutically acceptable salt or solvate thereof, to processes for their preparation, to pharmaceutical formulations containing them and to their use in medical therapy, particularly in the treatment of depression.

16 Claims, No Drawings

TETRAHYDROIMIDAZO[2,1-A] ISOQUINOLINE DERIVATIVES

FIELD OF THE INVENTION

The present invention relates to certain tetrahydroimidazo [2,1-a]isoquinoline derivatives, to processes for their preparation, to pharmaceutical formulations containing them and to their use in medical therapy, particularly in the treatment of depression.

BACKGROUND OF THE INVENTION

Depression is a common, serious and life threatening disorder, and its effects are persistent and debilitating.

The older antidepressants of the first generation, including imipramine and amitriptyline, have deleterious cardiovascular and anticholinergic side effects that can lead to serious toxicity in overdose and to poor patient compliance. The newer second generation drugs available from the mid-70's onwards, such as the atypical antidepressants and the inhibitors of serotonin reuptake (SSRI's), come with their own particular pattern of side effects which include sleep disturbances, gastrointestinal symptoms, sexual problems and anxiety. Lithium is plagued by a variety of adverse side effects, which often lead to poor compliance and subsequent relapse. The current alternatives to lithium, carbamazepine and valproate, are no more effective than lithium and carry the extra burden of haematological and hepatic toxicity respectively.

SUMMARY OF THE INVENTION

Because of the shortcomings of antidepressant drugs, the search for new agents continues. A new group of drugs have now been found which, apart from inhibiting the reuptake of serotonin, also inhibit the reuptake of noradrenaline and dopamine.

The dopamine reuptake inhibition is thought to produce a fast elevation of mood, which makes the compounds suitable for the acute relief of the symptoms of depression. This is considered to be a substantial advantage over known antidepressant drugs, such as the serotonin and noradrenaline reuptake blockers which have a delayed onset of action of two weeks or more.

Moreover, the present compounds are, in view of their ability to block the reuptake of dopamine, less sedative than the prior art compounds, and thus more appropriate in the treatment of patients with psychomotor retardation. Thus, the broader pharmacological profile of the compounds of the present invention will result in antidepressants which have a fast onset time, a broader efficacy spectrum and an advantageously reduced side effect profile. It is also believed that these compounds will be particularly effective in the treatment of the elderly, treatment resistant and bipolar depressed patients.

The compounds of the present invention may also be used for the treatment of Parkinson's disease, obesity, anxiety disorders, central pain, addiction and the negative symptoms in schizophrenic patients and a number of other disorders mentioned herein.

DETAILED DESCRIPTION OF THE INVENTION

According to one aspect, the present invention provides the compounds of formula (I):

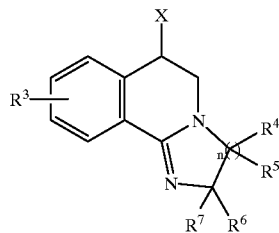

(I)

wherein X is a group (A) or (B)

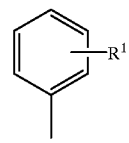

(A)

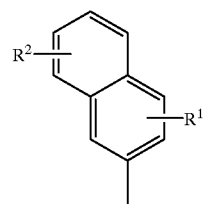

(B)

$R^1$, $R^2$ and $R^3$, which may be the same or different, each represent one or more substituents selected from hydrogen, $C_{1-6}$alkyl, $C_{3-6}$cycloalkyl, $C_{1-6}$alkoxy, $C_{1-6}$alkylthio, $C_{4-6}$cycloalkenyl, $C_{2-6}$alkenyl, $C_{2-6}$-alkynyl and halogen;

$R^4$, $R^5$, $R^6$ and $R^7$, which may be the same or different, are each selected from hydrogen, $C_{1-6}$-alkoxy$C_{1-6}$alkyl, $C_{4-6}$cycloalkenyl, $C_{2-6}$alkenyl, $C_{2-6}$alkynyl, $C_{3-6}$cycloalkyl and $C_{1-6}$alkyl;

n is 1 or 2;

or a pharmaceutically acceptable salt or solvate thereof for use in therapy.

In a further aspect of the invention there are provided the compounds of formula (I) and their pharmaceutically acceptable salts and solvates for use in in the treatment or prevention of depression or any of the diseases or disorders mentioned herein.

As used herein the term alkyl as a group or part of a group means a straight or branched chain alkyl group. The number of carbon atoms in the alkyl group (or in any of the other groups defined below) is indicated by a prefix, for example $C_{1-6}$alkyl means an alkyl group having from 1–6 carbon atoms. Such alkyl groups include methyl, ethyl, i-propyl, n-propyl, n-butyl, s-butyl, t-butyl, n-pentyl, isopentyl, neopentyl, n-hexyl, isohexyl and neohexyl. The term $C_{1-6}$alkylthio includes methylthio, ethylthio and propylthio.

References to alkenyl groups include groups which may be in the E- or Z-form or a mixture thereof and which when they contain at least three carbon atoms, may be branched. Examples of particular alkenyl groups include vinyl, allyl, butenyl, isobutenyl, pentenyl, isopentenyl, hexenyl, isohexenyl, neohexenyl and 1-methyl-2-propenyl. The terms alkoxy and alkynyl have meanings as understood by the person skilled in the art and include straight and branched chains. Examples of alkoxy groups include methoxy and ethoxy and examples of alkynyl groups include ethynyl, propynyl and butynyl.

As used herein the terms cycloalkyl and cycloalkenyl have meanings as understood by the person skilled in the art and include cyclopropyl, cyclobutyl, cyclobutenyl, cyclopentyl, cyclopentenyl, cyclopentadienyl, cyclohexyl, cyclohexenyl and cyclohexadienyl.

The term halogen includes chloro, bromo, fluoro and iodo.

Ring substituent $R^1$, when present in the phenyl group (A), may be in any one or more of the 2, 3, 4, 5 or 6 positions. Specific examples of single ring substituents includes 4-chloro or 4-fluoro. Examples of multiple substituents include 3-chloro, 4-fluoro and 3,4-dichloro. Ring substituent $R^1$, when present in the naphthyl group (B), may be in any one or more of the 1, 3 and 4 positions. Ring substituents $R^2$ and $R^3$ may be in any one or more of the positions available.

It will be appreciated that some of the compounds of formula (I) and their salts and solvates may contain one or more centres of chirality and exist as stereoisomers including diastereomers and enantiomers. The present invention includes the aforementioned stereoisomers within its scope and each of the individual (R) and (S) enantiomers of the compounds of formula (I) and their salts and solvates substantially free, ie associated with less than 5%, preferably less than 2%, in particular less than 1% of the other enantiomer and mixtures of such enantiomers in any proportions including racemic mixtures containing substantially equal amounts of the two enantiomers.

For therapeutic use, salts of the compounds of formula (I) are those acid addition salts wherein the acid is pharmaceutically acceptable. However, salts of acids which are non-pharmaceutically acceptable may also find use, for example, in the preparation or purification of a pharmaceutically acceptable compound. All salts, whether pharmaceutically acceptable or not are included within the ambit of the present invention.

Salts according to the invention include pharmaceutically acceptable acid addition salts derived from mineral acids such as hydrochloric, hydrobromic, hydroiodic, phosphoric, metaphosphoric, nitric and sulphuric acids, and those drived from organic acids, such as tartaric, acetic, trifluoroacetic, citric, malic, lactic, maleic (cis-butenedioic acid), malonic, fumaric, benzoic, ascorbic, propionic, glycolic, gluconic, succinic and methanesulphonic and arylsulphonic, for example ρ-toluenesulphonic acids. Preferred salts according to the invention include hydrochloric, oxalic, fumaric and maleic acid addition salts.

Solvates according to the invention include hydrates.

The compound (rac)-6-phenyl-2,3,5,6-tetrahydroimidazo [2,1-a]isoquinoline and processes for its manufacture are described in a synthetic study in J. Org Chem. 35, (4), 1178–1180, (1970). As a consequence no protection is sought for said compound per se.

Thus, according to a further aspect the present invention provides the compounds of formula (I) as defined above with the proviso that the compound is not (rac)-6-phenyl-2,3,5,6-tetrahydroimidazo[2,1-a]isoquinoline.

The following compounds of formula (I), either with or without the proviso thereto, represent preferred compounds according to the present invention:

(i) X is (A).
(ii) $R^1$ represents one or more substituents selected from hydrogen, $C_{1-6}$alkyl and halogen, preferably $R^1$ is in the 4-position (when X is (A)).
(iii) $R^3$, $R^4$, $R^5$, $R^6$ and $R^7$ are each hydrogen.
(iv) n is 1.
(v) X, $R^1$, $R^3$, $R^4$, $R^5$, $R^6$ and $R^7$ are as defined in points (i) to (iv) above; or a pharmaceutically acceptable salt or solvate thereof.

Particularly preferred compounds according to the invention, which have been found to be useful in the treatment of depression, are:

(rac)-6-(4-Chlorophenyl)-2,3,5,6-tetrahydroimidazo[2,1-a]isoquinoline;
(−)-6-(4-Chlorophenyl)-2,3,5,6-tetrahydroimidazo[2,1-a]isoquinoline;
(+)-6-(4-Chlorophenyl)-2,3,5,6-tetrahydroimidazo[2,1-a]isoquinoline;
(rac)-6-(4-Fluorophenyl)-2,3,5,6-tetrahydroimidazo[2,1-a]isoquinoline
(−)-6-(4-Fluorophenyl)-2,3,5,6-tetrahydroimidazo[2,1-a]isoquinoline;
(+)-6-(4-Fluorophenyl)-2,3,5,6-tetrahydroimidazo[2,1-a]isoquinoline;

and pharmaceutically acceptable salts and solvates thereof.

The present invention further includes a method for the treatment of an animal, for example, a mammal including a human, suffering from or liable to suffer from depression or any of the aforementioned disorders, which comprises administering an effective amount of a compound of formula (I) or a pharmaceutically acceptable salt or solvate thereof.

In yet a further aspect, the present invention provides the use of a compound of formula (I) or a pharmaceutically acceptable salt or solvate thereof in the manufacture of a medicament for the treatment or prevention of depression or any of the aforementioned diseases or disorders.

Depression states in the treatment of which the compounds of formula (I) and their pharmaceutically acceptable salts and solvates are particularly useful, are those classified as affective disorders in the Diagnostic and Statistical Manual of Mental Disorders. Fourth Edition-Revised, American Psychiatric Association, Washington, D.C. (1994), including the mood disorders, other specific affective disorders and bipolar and depressive disorders not otherwise specified.

Other uses in human therapy for the compounds of formula (I) or a pharmaceutically acceptable salt or solvate thereof includes the treatment of the following conditions:

anxiety disorders, including phobic neuroses, panic neuroses, anxiety neuroses, post-traumatic stress disorder and acute stress disorder.

attention deficit disorders.

eating disorders, including obesity, anorexia nervosa and bulimia.

personality disorders, including borderline personality disorders.

schizophrenia and other psychotic disorders, including schizo affective disorders, dilusional disorders, shared psychotic disorder, brief psychotic disorder and psychotic disorder.

narcolepsy-cataplexy syndrome.

substance related disorders.

sexual function disorders.

sleep disorders.

The amount of a compound of formula (I) or a pharmaceutically acceptable salt or solvate, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.01 to 125 mg per kilogram body weight of the recipient (e.g. a human) per day, preferably in the range of 0.1 to 50 mg per kilogram body weight per day and most preferably in the range 0.25 to 25 mg per kilogram body weight per day. The desired dose may be presented as one, two, three, four, five or more sub-doses administered at appropriate intervals throughout the day.

While it is possible for the active ingredient to be administered alone, it is preferable to present it as a pharmaceutical formulation. Accordingly, the present invention further provides a pharmaceutical formulation comprising a compound of formula (I) or a pharmaceutically acceptable salt or solvate thereof, together with a pharmaceutically acceptable carrier thereof and optionally other therapeutic agents. The carrier must be "acceptable" in the sense of being compatible with the other ingredients of the formulation and not deleterious to the recipients thereof.

Formulations include those suitable for oral, rectal, nasal, topical (including transdermal, buccal and sublingual), vaginal or parenteral (including subcutaneous, intramuscular, intravenous, intradermal and intravitreal) administration. The formulations may be prepared by methods well known in the art of pharmacy, for example, using methods such as those described in Gennaro et al., Remington's Pharmaceutical Sciences (18th ed., Mack Publishing company, 1990, see especially Part 8: Pharmaceutical Preparations and their Manufacture). Such methods include the step of bringing into association the active ingredient with the carrier which constitutes one or more accessory ingredients. Such accessory ingredients include those conventional in the art, such as, fillers, binders, diluents, disintegrants, lubricants, colorants, flavoring agents and wetting agents.

Formulations suitable for oral administration may be presented as discrete units such as pills, tablets or capsules each containing a predetermined amount of active ingredient; as a powder or granules; as a solution or suspension. The active ingredient may also be presented as a bolus or paste, or may be contained within liposomes, or in other formulations which provide for slow release of the active ingredient.

Formulations for rectal administration may be presented as a suppository or enema.

For parenteral administration, suitable formulations include aqueous and non-aqueous sterile injection. The formulations may be presented in unit-dose or multi-dose containers, for example, sealed vials and ampoules, and may be stored in a freeze dried (lyophilised) condition requiring only the addition of the sterile liquid carrier, for example, water prior to use.

Formulations suitable for administration by nasal inhalation include fine dusts or mists which may be generated by means of metered dose pressurised aerosols, nebulisers or insufflators.

The present invention further includes the following processes for the preparation of compounds of formula(I).

In the following description the symbols X, $R^1$, $R^2$, $R^3$, $R^4$, $R^5$, $R^6$ and $R^7$ have the meanings ascribed to them in formula (I) unless otherwise stated.

According to a first general process A, compounds of general formula (I) may be prepared by reacting compounds of general formula (II)

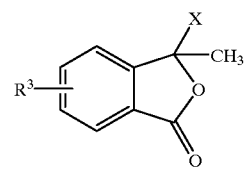

with ethylenediamine, or a derivative or chemical equivalent thereof. For example, the mono salts of ethylenediamine with various organic and in-organic acids can be used, preferably ethylenediamine p-toluenesulfonate (1:1). The reaction may be carried out in the presence of a solvent and at an elevated temperature, or typically in a melt at a temperature of approximately 200° C.

The intermediates of general formula (II) may be prepared by lactone formation by reacting a compound of formula (III)

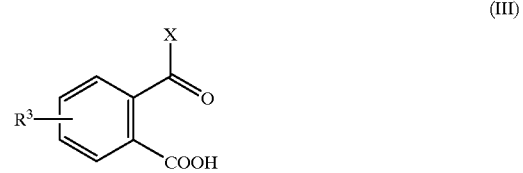

with an appropriate organometallic reagent, such as a lithium or zinc reagent and preferably a Grignard reagent, derived, for example, from $CH_3$-$L^1$, in which $L^1$ is a suitable leaving group, for example a halogen, such as a chlorine or bromine atom. Preferably methylmagnesium chloride or bromide is used in the presence of an apolar solvent such as hexane, diethyl ether or tetrahydrofuran, at a temperature of about −40° C. to 120° C., generally at reflux temperature.

Compounds of formula (III) may be prepared by methods described in the chemical literature or obtained commercially.

According to a second general process B, compounds of general formula (I) may be synthesised by cyclisation of intermediates of general formula (IV) in the presence of a dehydrating agent or acid catalyst, preferably concentrated sulphuric acid, at elevated temperatures such as 50° C.

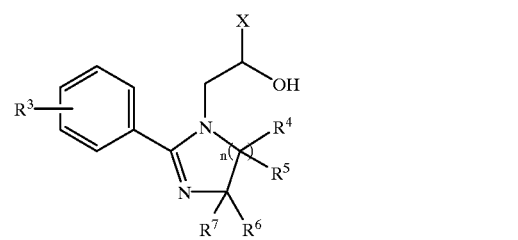

Intermediates of formula (IV) may conveniently be prepared by reduction of a ketone of formula (V) using methods known to those skilled in the art. Suitable reducing agents include hydrides such as lithium alkylborohydride, lithium aluminium hydride or borane or substituted boranes. The reaction may be carried out in an aprotic solvent such as diethyl ether and/or tetrahydrofuran. Other suitable hydrides include sodium borohydride in a polar solvent such as an alcohol at a temperature of −30° to 100° C.

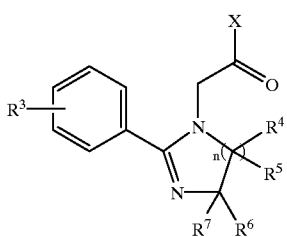

(V)

These compounds of general formula (V) can be obtained by reaction of intermediates (VI) with a phenacyl halide of choice, preferably after protection with triphenylmethyl chloride prior to reaction, which results in monoalkylated products (V).

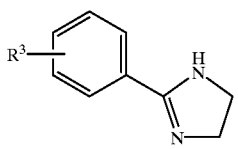

(VI)

Intermediates (VI) are readily available or can be obtained by reaction of the appropriately substituted benzonitriles with ethylenediamine, or a derivative or chemical equivalent thereof, with or without solvent at elevated temperatures.

The individual enantiomers of compounds of formula (I) may be obtained from the mixture of stereoisomers obtained by one of the sequences described above, using any method well known in the art. For example, using methods described in Stereochemistry of Organic Compounds, E. L. Eliel and S. H. Wilen, Chapter 7, 1994. In particular they may be obtained by conversion to diastereomers by methods such as salt formation with optically active acids followed by separation of the constituent diastereomers by fractional crystallisation or by differential absorption using columns packed with chiral material, for example preparative chiral liquid or gas chromatography.

Wherever one enantiomer is preferred the remaining fraction after the fractional crystallisation, mainly consisting of the other enantiomer, or the other enantiomer obtained, can be racemized by a suitable base like potassium hydroxide in an appropriate solvent such as dimethylsulfoxide at different temperatures, generally at room temperature and the resulting racemate can be resolved once more to raise the yield.

The final 6-aryl-2,3,5,6-tetrahydroimidazo[2,1-a] isoquinolines can be isolated as such or they can be converted into any desired acid addition salt or derivative. Most commonly an addition salt resulting from a pharmaceutically acceptable acid like hydrochloric acid, oxalic acid or fumaric acid is preferred.

Where necessary or desired, following one or more of the processes described above, any one or more of the following further steps in any order may be performed:

(i) removing any remaining protecting group(s);
(ii) converting a compound of formula (I) or a protected form thereof into a further compound of formula (I) or a protected form thereof;
(iii) converting a compound of formula (I) or a protected form thereof into a pharmaceutically acceptable salt or solvate of a compound of formula (I) or a protected form thereof;
(iv) converting a pharmaceutically acceptable salt or solvate of a compound of formula (I) or a protected form thereof into a compound of formula (I) or a protected form thereof;
(v) converting a pharmaceutically acceptable salt or solvate of a compound of formula (I) or a protected form thereof into another pharmaceutically acceptable salt or solvate of formula (I);
(vi) where the compound of formula (I) is obtained as a mixture of (R) and (S) enantiomers resolving the mixture to obtain the desired enantiomer.

The present invention further includes all novel intermediates and in particular the compounds of formulae (II), (IV) and (V). Specific intermediates according to the present invention include:

3-(4-Chlorophenyl)-3-methyl-1(3H)-isobenzofuranone;
3-(4-Fluorophenyl)-3-methyl-1(3H)-isobenzofuranone; and
3-(4-Methylphenyl)-3-methyl-1(3H)-isobenzofuranone.

The following examples are intended for illustration only and are not intended to limit the scope of the invention in any way.

EXAMPLE 1

3-(4-Chlorophenyl)-3-methyl-1(3H)-isobenzofuranone

Over a period of 30 minutes a solution of 130 g of 2-(4-chlorobenzoyl)benzoic acid in 300 ml of anhydrous tetrahydrofuran was added drop-wise under nitrogen to 900 ml of a stirred 3M solution of methylmagnesium chloride in anhydrous tetrahydrofuran. After the addition the reaction mixture was kept at reflux temperature for 1 hour. Afterwards it was cooled in an ice bath to room temperature and 1 L of an aqueous 2N sulfuric acid solution was added slowly, followed by 600 ml of toluene. The organic layer was separated and washed with brine, dried and evaporated in vacuo. Bulb to bulb destination (0.1 mm Hg/160° C.) afforded 60 g of 3-(4-chlorophenyl)- 3-methyl-1(3H)-isobenzofuranone as a yellow oil. M.S. (C.I.) (M/Z): 260 [M+H]$^+$.

In a similar way were prepared:
3-(4-Fluorophenyl)-3-methyl-1(3H)-isobenzofuranone M.S. (C.I.) (M/Z): 243 [M+H]$^+$, starting from 2-(4-fluorobenzoyl)benzoic acid,
3-(4-Methylphenyl)-3-methyl-1(3H)-isobenzofuranone M.S. (C.I.) (MIZ): 239 [M+H]$^+$, starting from 2-(4-methylbenzoyl)benzoic acid.
3-(2-Naphthyl)-3-methyl-1(3H)-isobenzofuranone M.S. (C.I.) (MIZ): 275 [M+H]$^+$, starting from 2-(2-naphthoyl) benzoic acid.

EXAMPLE 2

(rac)-6-(4-Chlorophenyl)-2,3,5,6-tetrahydroimidazo [2,1-a]isoguinoline hydrochloride A mixture of 60 g of 3-(4chlorophenyl)-3-methyl-1(3H)-isobenzofuranone and 257 g of ethylenediamine p-toluenesulfonate (166 ml ethylenediamine treated with 470 g p-toluenesulfonic acid and crystallised from 2-propanol) was heated to 200° C. and kept at this temperature overnight. The reaction mixture was allowed to cool and 850 ml of an aqueous 1N hydrochloride solution were added. The resulting mixture was extracted with 600 ml of chloroform. The organic layer was washed with 700 ml of an aqueous 1N potassium hydroxide solution, dried and evaporated in vacuo. The residue was crystallised from a 1:3 mixture of diethyl ether and hexane at −20° C. to give 46 g of (rac)-6-(4-chlorophenyl)-2,3,5,6-tetrahydroimidazo[2,1-a]isoquinoline as a yellow solid. The hydrochloride salt was prepared by the addition of a solution of hydrochloric acid in methanol resulting in (rac)6-(4-chlorophenyl)-2,3,5,6-tetrahydroimidazo[2,1-a]isoquinoline hydrochloride, melting point 230° C.

In a similar way were prepared:
(rac)-6-(4-Fluorophenyl)-2,3,5,6-tetrahydroimidazo[2,1-a]isoquinoline (Z)-2-butenedioate (1:1) salt, melting point 164° C., starting from 3-(4-fluorophenyl)-3-methyl-1(3H)-isobenzofuranone,
(rac)-2,3,5,6-Tetrahydro-6-(4-methylphenyl)imidazo[2,1-a]isoguinoline (Z)-2-butenedioate (1:1) salt, melting point 152° C., starting from 3-(4-methylphenyl)-3-methyl-1(3H)-isobenzofuranone.
(rac)-2,3,5,6-Tetrahydro-6-(2-naphthyl)imidazo[2,1-a]isoguinoline (E)-2-butenedioate (1:1) salt, melting point 216° C., starting from 3-(2-naphthyl)-3-methyl-1(3H)-isobenzofuranone.

EXAMPLE 3

(−)-6-(4-Chlorophenyl)-2,3,5,6-tetrahydroimidazo[2,1-a]isoguinoline (E)-2-butenedioate (1:1) salt To 40 g of 6-(4-chlorophenyl)-2,3,5,6-tetrahydroimidazo[2,1-a]isoquinoline were added 300 ml of ethanol and 30 ml of water along with 77 g of (+)-2-hydroxy-4-(2-methoxyphenyl)-5,5-dimethyl-1,3,2dioxaphosphorinane 2-oxide. The mixture was heated, resulting in a clear solution. Then it was cooled to room temperature and stirred for an additional hour. The solid formed was filtered and recrystallised from a mixture of 200 ml ethanol and 20 ml water to give 31 g of a product that was treated with an aqueous 1N potassium hydroxide solution and extracted with diethyl ether. The diethyl ether solution was dried, evaporated and the residue crystallised from hexane to give 9 g of (−)-6-(4-chlorophenyl)-2,3,5,6-tetrahydroimidazo[2,1-a]isoquinoline as a white solid with an enantiomeric excess found larger than 99%. A total of 8 g of (−)-6-(4-chlorophenyl)-2,3,5,6-tetrahydroimidazo[2,1-a]isoquinoline and 3,3 g of (E)-2-butenedioic acid were dissolved in 100 ml of hot 2-propanol and allowed to cool to room temperature. By filtration 10.9 g of (−)-6-(4-chlorophenyl)-2,3,5,6-tetrahydroimidazo[2,1-a]isoquinoline (E)-2-butenedioate (1:1) salt were isolated, melting point 184° C.

EXAMPLE 4

(+)-6-(4-Chlorophenyl)-2,3,5,6-tetrahydroimidazo[2,1-a]isoquinoline (E)-2-butenedioate (1:1) salt The remaining mother liquor obtained in Example 3 was evaporated in vacuo and heated in a mixture of aqueous 1N potassium hydroxide and toluene. The toluene layer was separated and evaporated in vacuo to afford 25 g of (+)-enantiomer enriched 6-(4-chlorophenyl)-2,3,5,6-tetrahydroimidazo[2,1-a]isoquinoline. This amount was dissolved in 200 ml of ethanol and 20 ml of water along with 45 g of (−)-2-hydroxy-4-(2-methoxyphenyl)-5,5-dimethyl-1,3,2-dioxaphosphorinane 2-oxide. The mixture was heated, resulting in a clear solution. After cooling to room temperature, a white solid precipitated, which was filtered off and recrystallised from ethanol/water 10:1. The solid obtained was partitioned between aqueous 1N potassium hydroxide and diethyl ether. The diethyl ether solution was evaporated and the residue crystallised from hexane to afford 7 g of (+)-6-(4-chlorophenyl)-2,3,5,6-tetrahydroimidazo[2,1-a]isoquinoline as a white solid with an enantiomeric excess found larger than 99%. The (E)-2-butenedioate (1:1) salt was prepared as described in Example 3, melting at 181° C.

EXAMPLE 5

(rac)-6-(4-Chlorophenyl)-2,3,5,6-tetrahydroimidazo[2,1-a]isoguinoline

In 100 ml of anhydrous dimethylsulfoxide were dissolved 14 g of (+)-enantiomer enriched 6-(4-chlorophenyl)-2,3,5,6-tetrahydroimidazo[2,1-a]isoquinoline with an enantiomeric excess of 87%. To this solution were added 6 g of powdered potassium hydroxide and the mixture was stirred overnight at room temperature. The reaction mixture was partitioned between water and diethyl ether and the organic layer was washed with brine, dried and evaporated to give 12 g of (rac)-6-(4-chlorophenyl)-2,3,5,6-tetrahydroimidazo[2,1-a]isoquinoline.

EXAMPLE 6

(−)-6-(4-Fluorophenyl)-2,3,5,6-tetrahydroimidazo[2,1-a]isoguinoline (E)-2-butenedioate (1:1) salt A total of 1.5 g of (rac)-6-(4-fluorophenyl)-2,3,5,6-tetrahydroimidazo-[2,1-a]isoquinoline was separated by chiral HPLC with a 95:5 mixture of hexane-ethanol 95:5 containing 0.2% of diethylamine, using a Chiracel™ OJ 50×2 cm column, at a temperature of 52° C. and a flow of 10 ml/min. Approximately every 18 minutes 120 mg (2×950 μl) were injected. The fractions eluting at 29,6 minutes were combined and evaporated to dryness under reduced pressure to yield 600 mg of a compound which was converted into its (E)-2-butenedioate (1:1) salt by the addition of one equivalent of (E)-2-butenedioic acid in methanol to yield (−)-6-(4-fluorophenyl)-2,3,5,6-tetrahydroimidazo[2,1-a]isoquinoline (E)-2-butenedioate (1:1) salt, enantio-purity >99,5%, melting at 205° C.

EXAMPLE 7

(+)-6-(4-Fluorophenyl)-2,3,5,6-tetrahydroimidazo[2,1-a]isoquinoline (E)-2-butenedioate (1:1) salt The second fractions of the chiral HPLC separation described under Example 6, eluting at 38 minutes, were combined and evaporated to dryness under reduced pressure to yield 590 mg of a compound which was converted into its (E)-2-butenedioate (1:1) salt by the addition of one equivalent of (E)-2-butenedioic acid in methanol to yield 600 mg of (+)-6-(4-fluorophenyl)-2,3,5,6-tetrahydroimidazo[2,1-a]isoquinoline (E)-2-butenedioate (1:1) salt, enantio-purity >99,5%, melting at 205° C.

EXAMPLE 8

In Vitro Activity

Measurement of dopamine (DUP), serotonin (SUP) and noradrenaline NUP) reuptake blockade was carried out using the methods described in Neuropharmacology Vol. 27, No. 3, pp. 251–260, 1988 and results are presented in Table 1 below.

TABLE 1

| EXAMPLE | NUP (pKi) | SUP (pKi) | DUP (pKi) |
|---------|-----------|-----------|-----------|
| 2a | 7.9 | 7.4 | 7.15 |
| 4 | 8.15 | 7.0 | 7.2 |
| 3 | 8.1 | 7.3 | 7.15 |
| 2b | 7.65 | 7.5 | 6.5 |
| 7 | 7.75 | 6.25 | 6.45 |
| 6 | 7.5 | 7.9 | 6.6 |
| 2c | 7.75 | 6.9 | 7.05 |

We claim:

1. A method for inhibiting the reuptake of dopamine, serotonin and noradrenalin in a patient suffering from a mental disorder, comprising administering to a patient in need thereof an effective amount of a compound of formula (I):

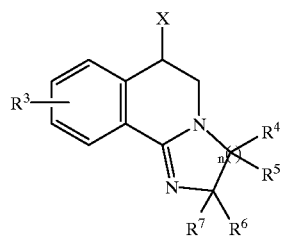

wherein X is a group (A) or (B)

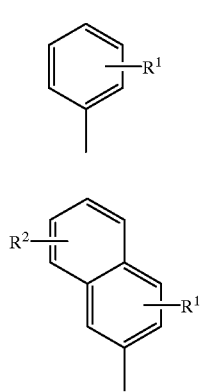

$R^1$, $R^2$ and $R^3$, which may be the same or different, each represent one or more substituents selected from hydrogen, $C_{1-6}$ alkyl, and halogen;

$R^4$, $R^5$, $R^6$ and $R^7$, which may be the same or different, are each selected from hydrogen and $C_{1-6}$ alkyl;

n is 1 or 2;

or a pharmaceutically acceptable salt or solvate thereof.

2. A method according to claim 1, wherein said mental disorder is depression.

3. A method according to claim 1, wherein X in formula (I) is (A).

4. A method according to claim 1, wherein $R^4$, $R^5$, $R^6$ and $R^7$ in formula I are each hydrogen.

5. A method according to claim 1, wherein in formula I n is 1.

6. A method according to claim 1, wherein said compound is selected from:

(rac)-6-(4-Chlorophenyl)-2,3,5,6-tetrahydroimidazo[2,1-a]isoquinoline;

(−)-6-(4-Chlorophenyl)-2,3,5,6-tetrahydroimidazo[2,1-a]isoquinoline;

(+)-6-(4-Chlorophenyl)-2,3,5,6-tetrahydroimidazo[2,1-a]isoquinoline;

(rac)-6-(4-Fluorophenyl)-2,3,5,6-tetrahydroimidazo[2,1-a]isoquinoline;

(−)-6-(4-Fluorophenyl)-2,3,5,6-tetrahydroimidazo[2,1-a]isoquinoline;

(+)-6-(4-Fluorophenyl)-2,3,5,6-tetrahydroimidazo[2,1-a]isoquinoline; and pharmaceutically acceptable salts or solvates thereof.

7. A pharmaceutical formulation comprising a compound of formula (I):

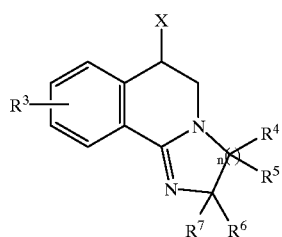

wherein X is a group (A) or (B)

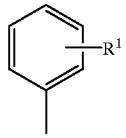

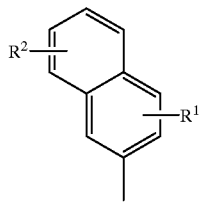

$R^1$, $R^2$ and $R^3$, which may be the same or different, each represents one or more substituents selected from hydrogen, $C_{1-6}$ alkyl, and halogen;

$R^4$, $R^5$, $R^6$ and $R^7$, which may be the same or different, are each selected from hydrogen and $C_{1-6}$ alkyl;

n is 1 or 2;

or a pharmaceutically acceptable salt or solvate thereof, together with a pharmaceutically acceptable carrier therefor.

8. A compound of formula (I):

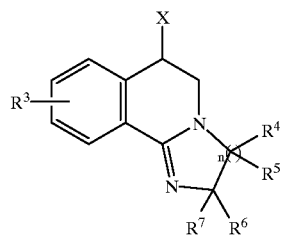
(I)

wherein X is a group (A) or (B)

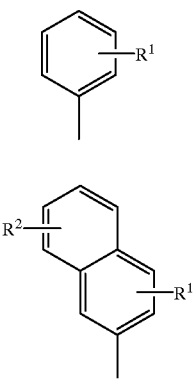

$R^1$, $R^2$ and $R^3$, which may be the same or different, each represent one or more substituents selected from hydrogen, $C_{1-6}$ alkyl and halogen;

$R^4$, $R^5$, $R^6$ and $R^7$, which may be the same or different, are each selected from hydrogen and $C_{1-6}$ alkyl;

n is 1 or 2;

or a pharmaceutically acceptable salt or solvate thereof;

with the proviso that the compound is not 6-phenyl-2,3,5,6-tetrahydroimidazo[2,1-a]isoquinoline.

9. A compound of formula (I) as defined according to claim 8, or a pharmaceutically acceptable salt or solvate thereof, wherein X in formula (I) is (A);

with the proviso that the compound is not 6-phenyl-2,3,5,6-tetrahydroimidazo[2,1-a]isoquinoline.

10. A compound selected from:
(rac)-6-(4-Chlorophenyl)-2,3,5,6-tetrahydroimidazo[2,1-a]isoquinoline;
(−)-6-(4-Chlorophenyl)-2,3,5,6-tetrahydroimidazo[2,1-a]isoquinoline;
(+)-6-(4-Chlorophenyl)-2,3,5,6-tetrahydroimidazo[2,1-a]isoquinoline;
(rac)-6-(4-Fluorophenyl)-2,3,5,6-tetrahydroimidazo[2,1-a]isoquinoline
(−)-6-(4-Fluorophenyl)-2,3,5,6-tetrahydroimidazo[2,1-a]isoquinoline;
(+)-6-(4-Fluorophenyl)-2,3,5,6-tetrahydroimidazo[2,1-a]isoquinoline;
and pharmaceutically acceptable salts and solvates thereof.

11. A method according to claim 1, wherein $R^1$ is in the 4 position.

12. A compound of formula (I) as defined according to claim 8 wherein $R^1$ is in the 4 position, or a pharmaceutically acceptable salt or solvate thereof;
with the proviso that the compound is not 6-phenyl-2,3,5,6-tetrahydroimidazo[2,1-a]isoquinoline.

13. A compound of formula (I) as defined according to claim 8, or a pharmaceutically acceptable salt or solvate thereof, wherein $R^4$, $R^5$, $R^6$ and $R^7$ in formula (I) are each hydrogen;
with the proviso that the compound is not 6-phenyl-2,3,5,6-tetrahydroimidazo[2,1-a]isoquinoline.

14. A compound of formula (I) as defined according to claim 8, or a pharmaceutically acceptable salt or solvate thereof, wherein in formula (I) n is 1;
with the proviso that the compound is not 6-phenyl-2,3,5,6-tetrahydroimidazo[2,1-a]isoquinoline.

15. A composition comprising a compound according to claim 8, together with a pharmaceutically acceptable carrier.

16. A process for preparing a composition, comprising bringing into association a compound according to claim 8 and a pharmaceutically acceptable carrier.

* * * * *

UNITED STATES PATENT AND TRADEMARK OFFICE
CERTIFICATE OF CORRECTION

PATENT NO. : 5,994,366
DATED : November 30, 1999
INVENTOR(S) : LEYSEN ET AL.

It is certified that error appears in the above-identified patent and that said Letters Patent is hereby corrected as shown below:

In Example 2, column 8, line 57, delete "[2,1-a]isoquinoline" and insert -- [2,1-a]isoquinoline --.

In Column 9, lines 11 - 12, delete "(rac)-6-(4-Fluorophenyl)-2,3,5,6-tetrahydroimidazo[2,1-a]isoquinoline (Z)-2-butenedioate (1:1) salt" and insert -- (rac)-6-(4-Fluorophenyl)-2,3,5,6-tetrahydroimidazo[2,1-a]isoquinoline (Z)-2-butenedioate (1:1) salt --;

lines 15 - 16, delete "(rac)-2,3,5,6-Tetrahydro-6-(4-methylphenyl)imidazo[2,1-a]isoquinoline (Z)-2-butenedioate (1:1) salt" and insert -- (rac)-2,3,5,6-Tetrahydro-6-(4-methylphenyl)imidazo[2,1-a]isoquinoline (Z)-2-butenedioate (1:1) salt --;

lines 19 - 20, delete "rac)-2,3,5,6-Tetrahydro-6-(2-naphthyl)imidazo[2,1-a]isoquinoline (E)-2-butenedioate (1:1) salt" and insert -- (rac)-2,3,5,6-Tetrahydro-6-(2-naphthyl)imidazo[2,1-a]isoquinoline (E)-2-butenedioate (1:1) salt --; and lines 26 - 27, delete "(-)-6-(4-Chlorophenyl)-2,3,5,6-tetrahydroimidazo[2,1-a]isoquinoline (E)-2-butenedioate (1:1) salt" and insert -- (-)-6-(4-Chlorophenyl)-2,3,5,6-tetrahydroimidazo[2,1-a]isoquinoline (E)-2-butenedioate (1:1) salt --.

Column 10, lines 11 - 12, delete "(rac)-6-(4-Chlorophenyl)-2,3,5,6-tetrahydroimidazo [2,1-a]isoquinoline" and insert -- (rac)-6-(4-Chlorophenyl)-2,3,5,6-tetrahydroimidazo [2,1-a]isoquinoline --; and lines 26 - 27, delete "(-)-6-(4-Fluorophenyl)-2,3,5,6-tetrahydroimidazo[2,1-a]isoquinoline (E)-2-butenedioate (1:1) salt" and insert -- (-)-6-(4-Fluorophenyl)-2,3,5,6-tetrahydroimidazo[2,1-a]isoquinoline (E)-2-butenedioate (1:1) salt --.

Signed and Sealed this

Fifteenth Day of August, 2000

Attest:

Attesting Officer

Q. TODD DICKINSON

Director of Patents and Trademarks